United States Patent [19]

Meier et al.

[11] Patent Number: 5,665,740

[45] Date of Patent: Sep. 9, 1997

[54] ISOPROPYL 2-METHOXYETHYL 4-(2-CHLORO-3-CYANO-PHENYL)-1,4-DIHYDRO-2,6-DIMETHYL-PYRIDINE-3,5-DICARBOXYLATE

[75] Inventors: Heinrich Meier, Kobe, Japan; Wolfgang Hartwig, Stamford, Conn.; Bodo Junge; Rudolf Schohe-Loop, both of Wuppertal, Germany; Zhan Gao, Beijing, China; Bernard Schmidt, Lindlar, Germany; Maarten de Jonge, Overath, Germany; Teunis Schuurman, Lohmar, Germany

[73] Assignee: Bayer Aktiengesellschaft, Leverkusen, Germany

[21] Appl. No.: 348,436

[22] Filed: Dec. 2, 1994

[30] Foreign Application Priority Data

Dec. 10, 1993 [DE] Germany .......................... 43 42 194.6
Jul. 13, 1994 [DE] Germany .......................... 44 24 677.3

[51] Int. Cl.⁶ .................. C07D 211/86; A61K 31/455
[52] U.S. Cl. .............................. 514/556; 546/321
[58] Field of Search ........................ 546/321; 514/356

[56] References Cited

U.S. PATENT DOCUMENTS

| | | | |
|---|---|---|---|
| 3,691,177 | 9/1972 | Bossert et al. | 546/321 |
| 3,764,683 | 10/1973 | Bossert et al. | 546/321 |
| 3,799,936 | 3/1974 | Meyer et al. | 546/321 |
| 3,932,646 | 1/1976 | Meyer et al. | 546/321 |
| 4,044,141 | 8/1977 | Bossert et al. | 546/321 |
| 4,406,906 | 9/1983 | Meyer et al. | 546/321 |
| 4,510,310 | 4/1985 | Wehinger et al. | 546/321 |
| 4,559,350 | 12/1985 | Wehinger et al. | 514/332 |
| 4,568,681 | 2/1986 | Wehinger et al. | 514/332 |
| 4,622,332 | 11/1986 | Wehinger et al. | 546/144 |
| 4,849,433 | 7/1989 | Wehinger et al. | 546/321 |
| 4,918,076 | 4/1990 | Opitz et al. | 546/321 |
| 4,956,361 | 9/1990 | Traber et al. | 514/217 |
| 4,988,717 | 1/1991 | Wehinger et al. | 546/321 |
| 5,114,946 | 5/1992 | Lawter et al. | 514/279 |
| 5,137,889 | 8/1992 | Tamada et al. | 514/364 |

FOREIGN PATENT DOCUMENTS

| | | |
|---|---|---|
| 151485 | 10/1970 | Australia . |
| 0451654 | 10/1991 | European Pat. Off. . |
| 0494816 | 7/1992 | European Pat. Off. . |
| 0525568 | 2/1993 | European Pat. Off. . |

OTHER PUBLICATIONS

CA 103:123371 1985.
Rampe D.R., Mutledge A., Janis R.A., Triggle D.J.: Can. Journ. Physiol. Pharmacol. 65, (1987) 1452.
Appel, Current Neurology vol. 6, pp. 289, 314, 315, Yearbook Medical Publishers Inc. 1987.
Clark et al. Principles of Psychopharmacology pp. 166 & 167, Academic Press 1970.

*Primary Examiner*—Jane Fan
*Attorney, Agent, or Firm*—Sprung Horn Kramer & Woods

[57] ABSTRACT

The present invention relates to the new compound rac-isopropyl 2-methoxyethyl 4-(2-chloro-3-cyano-phenyl)1,4-dihydro-2,6-dimethylpyridine-3,5-dicarboxylate and its pure enantiomers, processes for their preparation and their use as medicaments, in particular for the treatment of cerebral and neuronal disorders, and a new intermediate for their preparation.

4 Claims, No Drawings

ISOPROPYL 2-METHOXYETHYL 4-(2-CHLORO-3-CYANO-PHENYL)-1, 4-DIHYDRO-2,6-DIMETHYL-PYRIDINE-3,5-DICARBOXYLATE

The present invention relates to the new compound rac-isopropyl 2-methoxyethyl 4-(2-chloro-3-cyano-phenyl)-1,4-dihydro-2,6-dimethylpyridine-3,5-dicarboxylate and its pure enantiomers, processes for their preparation and their use as medicaments, in particular for the treatment of cerebral and neuronal disorders, and a new intermediate for their preparation.

It has already been disclosed that some 1,4-dihydropyridines such as e.g. nimodipine have cerebral activity [cf. German Offenlegungsschrift 2 815 578]. Dihydropyridine derivatives which in position 4 carry a phenyl ring which is optionally substituted by halogen and/or cyano are likewise described in general definitions and in some cases also as specific individual compounds (cf. German Offenlegungsschrift 1 963 188, German Offenlegungsschrift 2 117 573 and EP-A-026 317). However, in position 4 the specific 2-chloro-3-cyano-phenyl radical is not mentioned for any of the previously known dihydropyridines. This specific substituent in position 4, which is introduced by means of the likewise new 2-chloro-3-cyano-benzaldehyde via appropriate ring closure reactions, is an essential element of the present invention.

The present invention relates to the compound rac-isopropyl2-methoxyethyl4-(2-chloro-3-cyano-phenyl)-1,4-dihydro-2,6-dimethylpyridine-3,5-dicarboxylate of the formula (I)

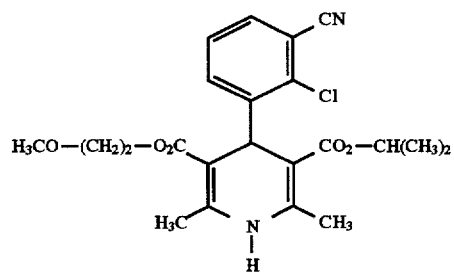

and its enantiomers.

The invention also relates to a plurality of processes for the preparation of the compound of the formula (I) according to the invention, which are characterized in that

[A] 2-chloro-3-cyano-benzaldehyde of the formula (II)

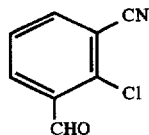

is reacted first with 2-methoxyethyl acetoacetate of the formula (III)

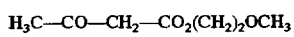

if appropriate with isolation of the corresponding ylidene compound of the formula (IV)

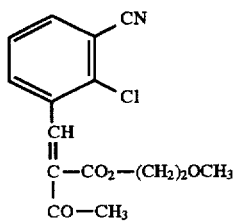

and subsequently with isopropyl acetoacetate of the formula (V)

$$CH_3—CO—CH_2—CO_2—CH(CH_3)_2 \quad (V)$$

and with ammonia or ammonium salts, or directly with the isopropyl amino-2-butenoate which can be prepared from ammonia and (V), of the formula (VI)

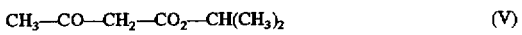

in inert solvents, or

[B] 2-chloro-3-cyano-benzaldehyde of the formula (II) is reacted first with the compound of the formula (V), if appropriate with isolation of the ylidene compound of the formula (VII)

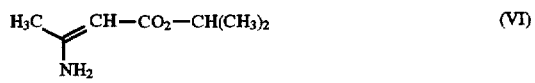

and in a next step with the compound of the formula (III) and with ammonia or ammonium salts or directly with the 2-methoxyethyl amino-2-butenoate which can be prepared from ammonia and (III), of the formula (VIII)

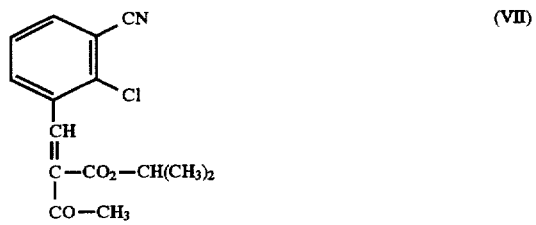

in inert solvents, or

[C] compounds of the general formula (IX)

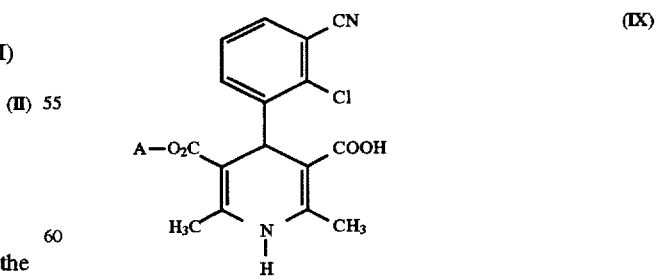

in which

A represents the radical of the formula —CH(CH₃)₂ or —(CH₂)₂—OCH₃, are reacted in inert solvents, if appropriate in the presence of a base, with auxiliaries to give activated carboxylic acid derivatives, which are optionally isolated, and then reacted with alcohols of the formula (X)

E—OH   (X)

in which

E depending on the definition of the substituent A, either represents the —CH(CH$_3$)$_2$— or —(CH$_2$)$_2$—OCH$_3$— group, if appropriate after conversion to the alkoxide using an inorganic base, and for the preparation of the enantiomers, the appropriate optically active carboxylic acid derivatives are reacted with the appropriate alcohols, or the racemate is separated by chromatography on chiral stationary phases.

The process according to the invention can be illustrated by way of example by the following reaction scheme:

[A]

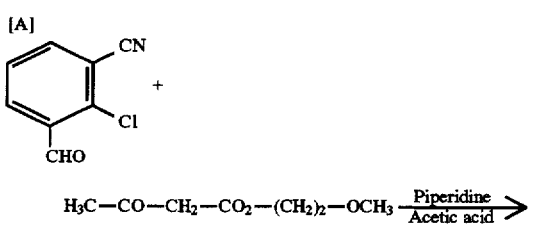

[B]

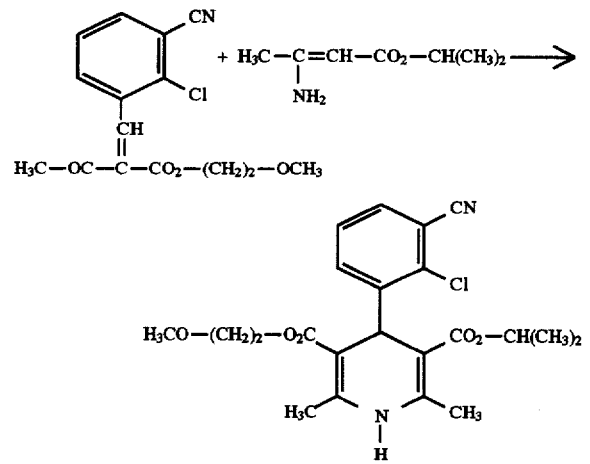

[C]

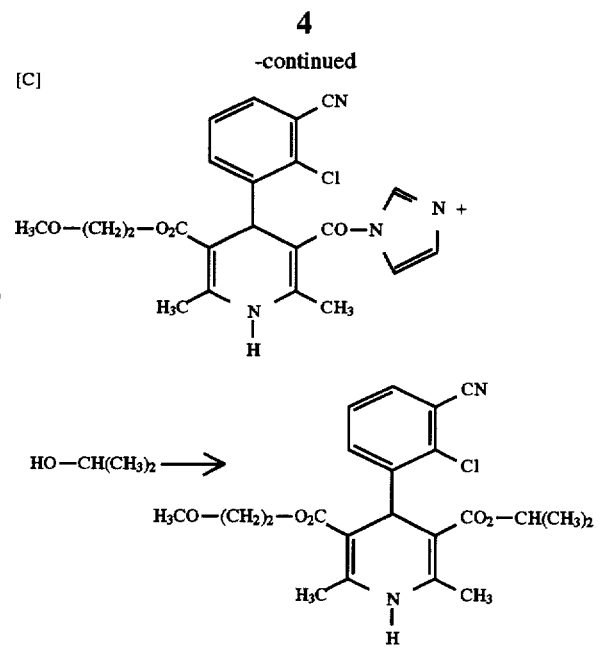

Suitable solvents for processes [A] and [B] here are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether, acetonitrile, or amides such as hexamethylphosphoramide or dimethylformamide, or acetic acid or halogenated hydrocarbons such as methylene chloride, carbon tetrachloride or hydrocarbons such as benzene or toluene. It is also possible to use mixtures of the solvents mentioned. Isopropanol, tetrahydrofuran, methanol, dioxane and dimethylformamide are particularly preferred.

Suitable solvents for process [C] are the abovementioned solvents with the exception of the alcohols and acetic acid.

Suitable bases for processes [A] and [B] are preferably cyclic amines, such as, for example, piperidine, $C_1$-$C_3$-tri- and dialkylamines, such as, for example, di- and triethylamine or pyridine or dimethylaminopyridine, in particular piperidine, dimethylaminopyridine and pyridine.

Condensing agents are preferably employed as auxiliaries for the activation of the carboxylic acid (IX). The customary condensing agents are preferred here, such as carbodiimides, e.g. N,N'-diethyl-, N,N'-dipropyl-, N,N'-disopropyl and N,N'-dicyclohexylcarbodiimide, N-(3-dimethylaminoisopropyl) -N'-ethylcarbodiimide hydrochloride, or carbonyl compounds such as carbonyldiimidazole, or 1,2-oxazolium compounds such as 2-ethyl-5-phenyl -1,2-oxazolium-3-sulphonate or 2-tert-butyl-5-methyl -isoxazolium perchlorate, or acylamino compounds such as 2-ethoxy-1-ethoxycarbonyl-1,2-dihydroquinoline, or propanephosphonic anhydride, or isobutyl chloro-formate, or benzotriazolyloxy-tris (dimethylamino)phosphonium hexafluorophosphonate. N,N'-dicyclohexylcarbodiimide and carbonyldiimidazole are preferred.

Suitable bases for variant [C] are alkali metal carbonates such as, for example, sodium carbonate or potassium carbonate, or organic bases such as trialkylamines, e.g. triethylamine, N-ethylmorpholine, N-methylpiperidine or diisopropylethylamide, or dimethylaminopyridine, 1,8-diazabicyclo[5.4.0]undec-7-ene (DBU) or 1,5-diazabicyclo [4.3.0]non-5-ene (DBN). Dimethylaminopyridine is preferred.

The base is in general employed in an amount from 0.01 mol to 1 mol, preferably from 0.05 mol to 0.1 mol, in each case relative to 1 mol of compound of the formula (IX).

The auxiliaries according to variant [C] are in general employed in an amount from 1 mol to 3 mol, preferably from 1 mol to 1.5 mol, in each case relative to 1 mol of the compound of the formula (IX).

Inorganic bases according to [C] employed are alkali metals or their hydrides. Sodium and sodium hydride are preferred. The inorganic bases according to process [C] are in general employed in an amount from 0.1 to 10 mol, preferably 0.2 to 2 mol, relative to 1 mol of the compound of the formula IV.

The reaction temperature for the processes [A], [B] and [C] can be varied within a relatively wide range. In general, the reaction is carried out in a range from −20° C. to 200° C., preferably from 0° C. to 110° C.

The processes can be carried out at normal pressure, elevated or reduced pressure (for example from 0.5 to 5 bar), preferably at normal pressure.

When carrying out the process according to the invention the ratio of the substances participating in the reaction is arbitrary. In general, however, the reaction is carried out with molar amounts of the reactants.

Enantiomeric pure forms are additionally obtained e.g. by separating the racemate on chromatographic columns having a chiral stationary phase.

The reactive acid derivatives of the general formula (IX) are known in some cases or are new and can then be prepared according to customary methods.

The compounds of the general formula (X) are known.

The ylidene compound of the formula (IV) is new and can be prepared, for example, as described above.

The ylidene compound of the formula (VII) is new and can be prepared, for example, as described under [A] by reaction of the compound of the formula (V) with 2-chloro-3-cyano-benzaldehyde of the formula (II).

The compounds of the formula (III), (V), (VI) and (VIII) are known per se.

2-chloro-3-cyano-benzaldehyde of the formula (II) is new and can be prepared, for example, by converting 2-chloro-3-cyano-toluene of the formula (XI)

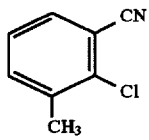

(XI)

first by bromination in the presence of a catalyst in inert solvents and under a protective gas atmosphere and irradiation to the compound 2-chloro3-cyano-benzal bromide of the formula. (XII)

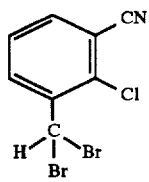

(XII)

and in a second step treating the crude products with silver salts in alcoholic solution and reacting to give the aldehyde.

Suitable solvents for the first step of the reaction are preferably the abovementioned halogenohydrocarbons such as dichloromethane or carbon tetrachloride. Carbon tetrachloride is particularly preferred.

Suitable brominating agents are preferably N-bromosuccinimide or bromine. N-bromosuccinimide is particularly preferred.

Suitable solvents for the second step of the process are water or the abovementioned alcohols such as, for example, methanol, ethanol, propanol or isopropanol or their mixtures. Ethanol is preferred.

Suitable catalysts are, for example, azoisobutyronitrile or bisbenzoyl peroxide. Azoisobutyronitrile is preferred.

The catalyst is in general employed in an amount from 0.0005 mol to 0.05 mol, preferably from 0.005 mol to 0.02 mol, relative to 1 mol of the compound of the formula (XI).

N-Bromosuccinimide is employed in an amount from 2 mol to 5 mol, preferably from 2.2 mol to 3 mol, relative to 1 mol of the compound of the formula (XI).

The bromination is carried out in a temperature range from 40° C. up to the respective reflux temperature of the solvent, preferably at the reflux temperature.

The conversion to the aldehyde is carried out in a temperature range from 20° C. to 100° C., preferably from 40° C. to 70° C.

The reactions are in general carried out at normal pressure. However, it is also possible to work at elevated or reduced pressure (e.g. in a range from 0.5 to 5 bar).

Suitable silver salts are in general salts such as silver nitrate, silver carbonate or silver tetrafluoroborate. Silver nitrate is preferred.

2-Chloro-3-cyano-toluene of the formula (XI) is known (CAS 15015-71-5).

2-Chloro-3-cyano-benzal bromide of the formula (XII) is new and can be prepared, for example, as described above.

The above preparation processes are only given for clarification. The preparation of the compound of the general formula (I) and its enantiomers is not restricted to these processes, but any modification of these processes and customary alternative processes are applicable in the same manner for the preparation of the compound according to the invention.

The compound according to the invention and its pure enantiomers exhibit an unpredictable, useful spectrum of pharmacological action. They have a positive effect on learning and memory powers, as their memory-enhancing effects in typical learning and memory models such as the water maze, passive avoidance or memory tests in automated Skinner boxes demonstrates. They have an antidepressant potential, as their activity in the rat swimming test according to Porsolt confirms.

Binding assays:

The binding affinities to PN 200-110 binding sites in rat brains or rat hearts were determined according to Ramp D. R., Mutledge A., Janis R. A., Triggle D. J.: Can. Journ. Physiol. Pharmacol. 65, (1987) 1452.

Water maze:

Old Wistar rats are placed in the starting position in a plastic tank filled with cold water and subdivided by vertical barriers. In order to reach a ladder which enables the animals to escape from the water, they must swim around these barriers. The time which is required for finding the exit and the number of errors on the way there are recorded. In this case, an error is defined as swimming up a blind alley or swimming over the boundary of imaginary squares into which the tank is subdivided in the direction away from the exit.

The rats remain in the maze until finding the exit, but at longest 300 sec. They are then taken out, dried and warmed under a red light. They then return to their home cages.

In a typical experiment, two equivalent animal groups (placebo, test substance each n=15) are determined by means of a preliminary test. The animals then go through 6 test sessions, two per day. Test substances or placebo are administered orally 30 min before the experiments. The measure of the learning—and memory-enhancing effect of the test substances in comparison to placebo is reduction of the time until reaching the exit, reduction of the number of errors and increase in the number of animals which find the exit at all.

Rat swimming test according to Porsolt

During a preliminary test, young rats are placed in a glass cylinder (40 cm high, 20 cm diameter) which is filled 17 cm high with water at 25° C. After 20 min in the water, the animals are taken out and warmed under a lamp for 30 min. In this preliminary test, all rats attempt to get out of the cylinder until after about 15 min they remain immobile ("behavioural despair", giving-up behaviour). 24 h later, the test session starts in which the rats are placed in the glass cylinder as on the previous day, but this time for only 5 min. The lengths of time for which the rats remain immobile during this 5 min are recorded. In this case, a rat is regarded as immobile which, floating upright in the water, only carries out minimal movements in order to keep its head above water. The antidepressant effect of the test substances is seen in the reduction of the period of immobility in comparison to the placebo values.

The compound according to the invention and its pure enantiomers are superior to known dihydropyridines in their effectiveness on learning and memory. Thus, for example, (+)-isopropyl 2-methoxyethyl 4-(2-chloro-3-cyanophenyl)-1,4-dihydro-2,6-dimethyl-pyridine-3,5-dicarboxylate in the water maze animal model (old rats) significantly improves acquisition in the range from 0.1 to 1.0 mg/p.o., while nimodipine only acts at 15 mg/kg p.o. At the same time, the compound according to the invention does not show any or shows a distinctly weaker blood pressure decrease than known compounds such as e.g. nimodipine. In the normotensive rat animal model, nimodipine decreases the blood pressure at 30 mg/kg p.o. approximately 3×more strongly than (+)-isopropyl 2-methoxyethyl 4-(2-chloro-3-cyanophenyl)-1,4-dihydro-2,6-dimethyl-pyridine-3,5-dicarboxylate; the same is found in the spontaneously hypertensive rat animal model (3 and 10 mg/kg p.o.). In the case of the compound according to the invention, a more potent specific CNS effect is therefore to be expected with a smaller—undesired—effect on the cardiovascular system.

As a result of its pharmacological properties, the compound can be employed for the preparation of medicaments for the treatment of central degenerative disorders, as, for example, occur in dementias (multi-infarct dementia, MID, primary degenerative dementia PDD, pre- and senile Alzheimer's disease, HIV dementia and other forms of dementia), Parkinson's disease or tropic lateral sclerosis.

It is furthermore suitable for the treatment of cerebral function disorders in old age, of organic brain syndrome (OBS) and of age-associated memory impairment (AAMI).

It is useful for the prophylaxis and for the control of the sequelae of cerebral circulatory disorders such as cerebral ischaemias, strokes and of subarachnoid haemorrhages.

It is suitable for the treatment of depressions and of mania. Further areas of application are the treatment of migraine, of neuropathies, which are caused e.g. by metabolic disorders such as diabetes mellitus, traumas, intoxifications, microorganisms or autoimmune disorders, of addictive disorders and withdrawal symptoms.

The present invention also includes pharmaceutical preparations which, in addition to inert, non-toxic, pharmaceutically suitable auxiliaries and excipients, contain the compound of the general formula (I), and processes for the production of these preparations.

The active compound of the formula (I) should be present in these preparations in a concentration of 0.1 to 99.5% by weight, preferably of 0.5 to 95% by weight of the total mixture.

In addition to the active compound of the formula (I), the pharmaceutical preparations can also contain other pharmaceutical active compounds.

The abovementioned pharmaceutical preparations can be prepared in a customary manner by known methods, for example using the excipient(s) or auxiliary(-ies).

In general, it has proven advantageous to administer the active compound of the formula (I) in total amounts of about 0.01 to about 50 mg/kg, preferably in total amounts of about 0.1 mg/kg to 10 mg/kg of body weight every 24 hours, if appropriate in the form of several individual doses, to achieve the desired result.

However, it may sometimes be advantageous to deviate from the amounts mentioned, namely depending on the type and the body weight of the subject treated, on individual behaviour towards the medicament, the nature and severity of the disorder, the type of preparation and administration, and the time and interval at which administration takes place.

The $R_f$ values shown in each case were determined—if not stated otherwise—by thin layer chromatography on silica gel (aluminium foil, silica gel 60 F 254, E. Merck). The substance spots were visualized by observation under UV light and/or by spraying with 1% strength potassium permanganate solution or with molybdataophosphoric acid solution.

Flash chromatography was carried out on silica gel 60, 0.040–0.064 mm, E. Merck. Elution with solvent gradients means: starting with the pure, non-polar solvent mixture component, the polar eluent component is admixed to an increasing extent until the desired product is eluted (TLC checking). With all products, the solvent was distilled off at finally about 0.1 mm Hg.

Starting compounds

EXAMPLE I

2-Methoxyethyl 2-acetyl-3-(2-chloro-3-cyano)-2-propenoate

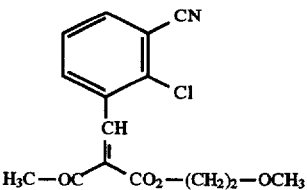

0.5 ml of piperidine and 0.3 ml of glacial acetic acid, dissolved in 4 ml of Isopropanol, are added to 13.0 g (78.5 mmol) of 2-chloro-3-cyanobenzaldehyde and 13.8 g (86 mmol) of 2-methoxyethyl acetoacetate in 130 ml of isopropanol. After stirring overnight at 40° C., the mixture is concentrated, the residue is taken up in toluene and the solution is filtered through silica gel $K_{60}$ (solvent: toluene/ethyl acetate gradient 1:0 to 10:1). After evaporating, 16.3 g of yellowish oil are obtained which is reacted further without further purification.

EXAMPLE II

2-Chloro-3-cyano-benzal bromide

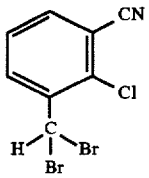

100 g (0.66 mol) of 2-chloro-3-cyano-toluene (CAS 15013-71-5) are dissolved in 1.0 l of carbon tetrachloride under argon and treated with 280 g (1.6 mol) of N-bromosuccinimide and 0.65 g of azoisobutyronitrile. The mixture is heated to reflux with vigorous stirring; during the course of this it is irradiated with a lamp (300 W, Osram Ultra-Vitalux$^R$). After 21 h and after 36 h, a further 50 g of N-bromosuccinimide and 0.5 g of azoisobutyronitrile are added each time. The reaction is complete after a total of 60 h. After cooling, insoluble material is filtered off; the precipitate is subsequently washed several times with carbon tetrachloride and discarded. After concentrating the filtrate, 180 g of the title compound are thus obtained as a crude product (according to. HPLC contains about 2% of corresponding benzyl bromide and 1.2% of corresponding benzotribromide).

EXAMPLE III

2-Chloro-3-cyano-benzaldehyde

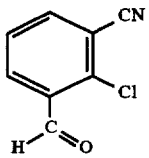

The crude product of the compound from Example II is dissolved in 1.5 l of 95% ethanol and warmed to 60° C. A solution of 186 g (1.1 mol) of silver nitrate in 380 ml of water which has been mixed with 750 ml of ethanol is rapidly added dropwise thereto at this temperature. After addition is complete, the mixture is subsequently stirred for one hour and then mixed with 50 ml of saturated sodium chloride solution. After cooling, the silver salts are filtered off and the filtrate is concentrated. The residue is taken up in methylene chloride and purified by filtration through a short silica gel column (eluent: dichloromethane). After concentrating the product fractions, 88 g (81%) of the title compound are obtained.

m.p.: 86°–89° C.

$^1$H-NMR (CHCl$_3$): δ=7.55 ppm (t, 1H); 7.95 (dd, 1H); 8.20 (dd, 1H); 10.5 (s, 1H).

Preparation examples

EXAMPLE 1 rac-Isopropyl 2-methoxyethyl 4-(2-chloro-3-cyano-phenyl)1,4-dihydro-2,6-dimethyl-pyridine-3,5-dicarboxylate

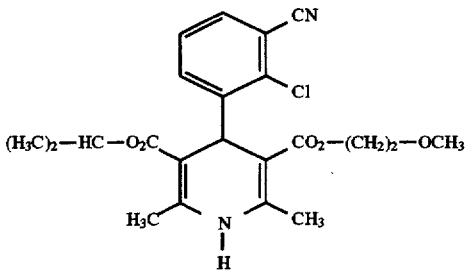

18.6 g (60.5 mmol) of the compound from Example I and 8.7 g (60.5 mmol) of isopropyl amino-2-butenoate in 250 ml of isopropanol are heated at reflux for 4 h. After concentrating, a solid is obtained which is digested with ether (18.1 g). This is mixed with the same amount of cyclohexane in 180 ml of toluene at boiling heat. After cooling to room temperature, crystals are obtained which are dried at 80° C. in a recirculating air drying oven.

Yield: 17.6 g (67%)

M.p.: 148°–149° C.

EXAMPLE 2 AND EXAMPLE 3

(+)-rac-Isopropyl 2-methoxyethyl 4-(2-chloro-3-cyano-phenyl)-1,4-dihydro-2,6-dimethyl-pyridine-3,5-dicarboxylate (−)-rac-Isopropyl 2-methoxyethyl 4-(2-chloro-3-cyano-phenyl)-1,4-dihydro-2,6-dimethyl-pyridine-3,5-dicarboxylate

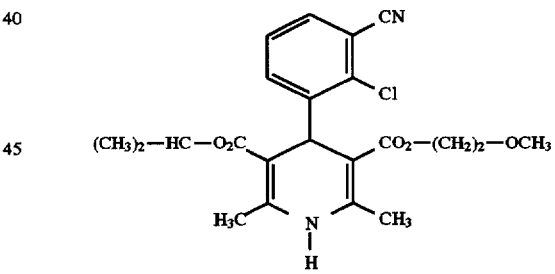

The pure enantiomers of Example 1 can he obtained by chromatography on chiral columns (e.g. Chiracel$^R$ OD-H, eluent 95% n-heptane/5% mixture of 1% water/0.2% trifluoroacetic acid in ethanol).

EXAMPLE 2

M.p.: 138°–140° C.

[α]$_D^{20}$=+13.9 (c=1, CHCl$_3$)

EXAMPLE 3

M.p.: 138°–140° C.

[α]$_D^{20}$=12.1 (c=0.9, CHCl$_3$)

We claim:

1. Isopropyl 2-methoxyethyl 4-(2-chloro-3-cyano-phenyl)-1,4-dihydro-2,6-dimethyl-pyridine-3,5-dicarboxylate as a racemate or as its enantiomeric form.

2. A process for the preparation of a compound according to claim 1, which comprises first reacting a compound of the formula

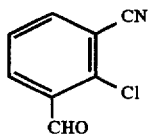

(II)

with 2-methoxyethyl acetoacetate of the formula $$H_3C-CO-C_2-CO_2(CH_2)_2OCH_3 \quad \text{(III)}$$

optionally, with isolation of the corresponding ylididene of the formula

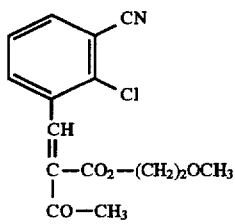

(IV)

and subsequently either reacting the product formed above with isopropyl acetoacetate of the formula $$CH_3-CO-CH_2-CO_2-CH(CH_3)_2 \quad \text{(V)}$$

in the presence of ammonia or ammonium salts or reacting the product formed in step 1 directly with isopropyl amino-2-butenoate

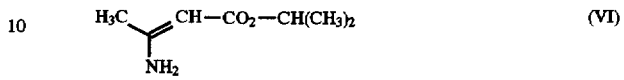

(VI)

in the presence of inert solvents wherein the amino-2-butenoate is optionally prepared from the reaction of ammonia and isopropyl acetoacetate.

3. A method of treating dementia in a patient in need thereof which comprises administering to said patient an effective amount of a compound according to claim 1.

4. A method of treating depression in a patient in need thereof which comprises administering to said patient an effective amount of a compound according to claim 1.

* * * * *

UNITED STATES PATENT AND TRADEMARK OFFICE
CERTIFICATE OF CORRECTION

PATENT NO. : 5,665,740
DATED : September 9, 1997
INVENTOR(S) : Meier, et al.

It is certified that error appears in the above-identified patent and that said Letters Patent is hereby corrected as shown below:

Col. 11, line 11  Delete " $H_3C-CO-C_2-CO_2(CH_2)_2OCH_3$ " and substitute -- $H_3C-CO-CH_2-CO_2(CH_2)_2OCH_3$ --

Signed and Sealed this

Fourth Day of January, 2000

Attest:

Attesting Officer

Acting Commissioner of Patents and Trademarks